(12) United States Patent
Kim et al.

(10) Patent No.: US 11,141,280 B2
(45) Date of Patent: Oct. 12, 2021

(54) ARTIFICIAL HIP JOINT STEM AND STEM PROVIDING METHOD

(71) Applicant: KCIS CO., LTD., Goyang-si (KR)

(72) Inventors: Doo Man Kim, Gwangmyeong-si (KR); Hyun Duk Kim, Seoul (KR)

(73) Assignee: KCIS CO., LTD., Goyang-si (KR)

( * ) Notice: Subject to any disclaimer, the term of this patent is extended or adjusted under 35 U.S.C. 154(b) by 258 days.

(21) Appl. No.: 16/341,030

(22) PCT Filed: Jan. 2, 2017

(86) PCT No.: PCT/KR2017/000012
§ 371 (c)(1),
(2) Date: Apr. 10, 2019

(87) PCT Pub. No.: WO2018/074667
PCT Pub. Date: Apr. 26, 2018

(65) Prior Publication Data
US 2019/0231540 A1 Aug. 1, 2019

(30) Foreign Application Priority Data
Oct. 19, 2016 (KR) .................. 10-2016-0135826

(51) Int. Cl.
*A61F 2/36* (2006.01)
*A61F 2/46* (2006.01)
*A61F 2/30* (2006.01)

(52) U.S. Cl.
CPC .............. *A61F 2/3609* (2013.01); *A61F 2/30* (2013.01); *A61F 2/36* (2013.01); *A61F 2/367* (2013.01); *A61F 2/4657* (2013.01); *A61F 2002/3625* (2013.01); *A61F 2002/3674* (2013.01); *A61F 2002/4668* (2013.01)

(58) Field of Classification Search
CPC .......... A61F 2/3609; A61F 2/367; A61F 2/30; A61F 2/36
See application file for complete search history.

(56) References Cited

U.S. PATENT DOCUMENTS

| 8,252,061 B2 | 8/2012 | Mikami et al. |
| 9,572,682 B2 | 2/2017 | Aghazadeh |
| 2013/0253658 A1 | 9/2013 | Despres et al. |

FOREIGN PATENT DOCUMENTS

| CN | 204526295 U | 8/2015 |
| KR | 10-1997-0704389 A | 9/1997 |

(Continued)

*Primary Examiner* — Jason-Dennis N Stewart
(74) *Attorney, Agent, or Firm* — Maschoff Brennan (57) ABSTRACT

An artificial hip joint stem is used to replace the damaged femoral head or acetabulum and includes a stem body having a head fixing part, which fixes a head, and an operating space horizontally opened at the upper side thereof. A head insertion hole connects to the operating space. A screw part is inserted into the head insertion hole. An operation converting part is inserted into the operating space to vertically move by the screw part when the operation converting part is connected to the screw part. A fixing bracket is inserted into the operating space such that the screw part is fixed to rotate without changing the depth thereof. A variable operating part is inserted into a supporting surface of the stem body to adjust a horizontal width by means of the operation converting part. A movable pin fixes the variable operating part to the operation converting part.

20 Claims, 7 Drawing Sheets

(56) References Cited

FOREIGN PATENT DOCUMENTS

| | | |
|---|---|---|
| KR | 10-2004-0060127 A | 7/2004 |
| KR | 10-2005-0100511 A | 10/2005 |
| KR | 10-2005-0100512 A | 10/2005 |
| KR | 10-2006-0089406 A | 8/2006 |
| KR | 10-2008-0084930 A | 9/2008 |
| KR | 10-2012-0062706 A | 6/2012 |
| KR | 10-2012-0085239 A | 7/2012 |
| KR | 10-2014-0128939 A | 11/2014 |

ARTIFICIAL HIP JOINT STEM AND STEM PROVIDING METHOD

TECHNICAL FIELD

The present invention relates to an artificial hip joint stem and a stem providing method, and more particularly, to an artificial hip joint stem that is inserted into a femur and has a structure that is separable, contractible and expandable so that an impact applied to the femur through the stem can be minimized when the stem is inserted into the femur and the stem can be easily removed, and a stem providing method.

BACKGROUND ART

A hip joint is a joint connecting the pelvis to a femur that is placed between the acetabulum of the pelvis and the femoral head and corresponds to a shoulder joint of the upper limb. Since the round femoral head is caught in the acetabulum, the hip joint belongs to spheroidal joints.

The hip joints are often used to cause cartilage damage between the femoral head and the acetabulum, resulting in inflammation, which is usually referred to as hip osteoarthritis.

Current treatments of hip osteoarthritis include local injection of NSAID dir, hyaluronic acid, or glucocorticoids to assist in lubrication of the hip joint and to assist in replacing the portion of the hip joint with an artificial organ through hip surgery.

In addition, when the hip joint becomes unusable due to fracture or degeneration, it is treated through joint replacement surgery. Anatomically, the buttock has a spherical joint, and the "ball," namely, the femur joint, is inserted into a cup-shaped socket of the pelvis. Thus, when these bones suffer ossifluence or are broken, a hip joint implant is surgically inserted to replace the damaged natural bone and cartilage of the hip.

Figure 1:
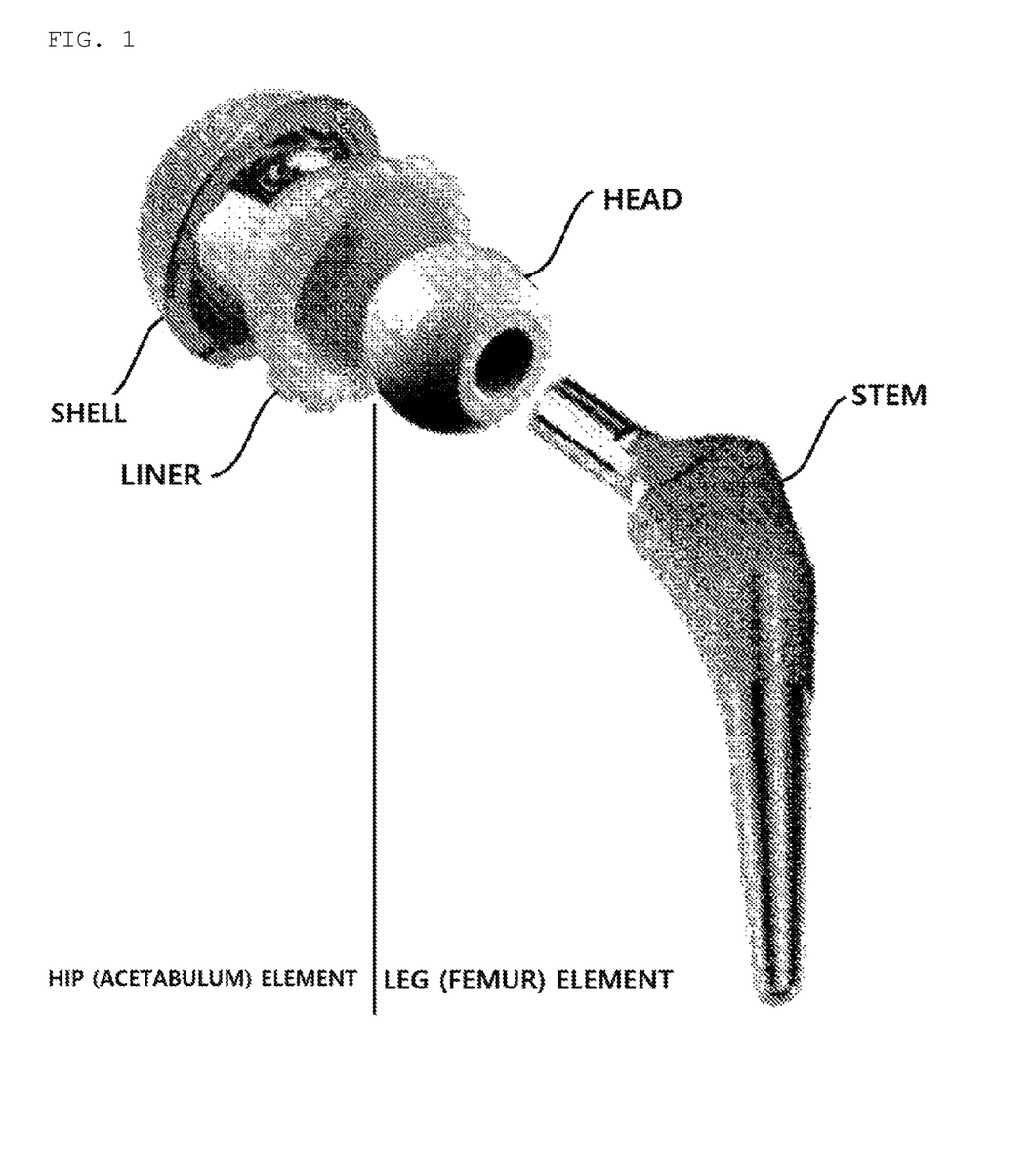
FIG. 1 is a photograph showing a conventional artificial hip joint.

Essentially, the hip joint implant has four different parts in structure as shown in FIG. 1.

An acetabular implant, also known as an acetabular "cup" or "shell," to replace a natural acetabulum (heap socket), includes a liner generally made of polyurethane, ceramic or metal to cover the inner surface of the cup, a metal stem inserted into the shaft of the natural femur to replace the neck of the femur to provide stability and movement for a reconstructed joint, and a metal or ceramic ball to replace the neck of the natural femur.

In order for such artificial hip joint to replace the existing femoral head and acetabulum, the femoral head is partially cut, a hole is drilled in the cut femoral head, and the stem is fixedly inserted into the hole. A part of the acetabulum of the pelvic bone is also cut and replaced with the shell.

In addition, in the conventional cases, when the stem is to be inserted into the femur, a hole is formed in the femur to have a smaller diameter than the outer diameter of the stem, such that the stem is inserted and coupled into the femur in a press-fitting manner.

However, when the stem is fixed to the femur by the conventional method of inserting the stem, a strong impact is applied to the femur by the press-fitting. Thus, when the bone density of the femur is weak, as in the case of the elderly, the femur can be damaged in the process of inserting the stem.

That is, in order for the artificial hip joint to maintain the initial strong fixation power, it is necessary to increase adhesion to the femur, and thus the hole of the femur is formed to be smaller than the diameter of the stem, which causes a problem.

Further, while the hole formed in the femur should be smaller than the stem, and the stem should be press-fit to the hole, not all holes are substantially formed to be small. As a result, the operation often fails due to a hole larger than the stem.

In addition, since re-operation needs to be considered according to the service life of the artificial hip, a method for removing the artificial hip joint should be sought. In conventional cases, however, it is very difficult to remove the installed artificial hip joint.

This is because the installed artificial hip joint is fixed to the bone as the bone grows over time. Or, it is very difficult to separate the artificial hip joint from a patient who has undergone operation for the artificial hip joint when the patient undergoes reoperation due to osteolysis.

Korean Patent Application Publication Nos. 10-2005-0100511, 10-2005-0100512 and 10-2008-0084930 disclose conventional artificial hip joints, and Korean Patent Application Publication Nos. 10-2012-0085239, 10-2012-0062706 and 10-2014-0128939 disclose operation methods. The disclosed conventional techniques have the above-mentioned problems.

DISCLOSURE

Technical Problem

Therefore, the present invention has been made in view of the above problems, and it is one object of the present invention to provide an artificial hip joint stem that is to inserted into a femur and has a structure that is separable, contractible and expandable so that an impact applied to the femur through the stem can be minimized when the stem is inserted into the femur and the stem can be easily removed, and a stem providing method thereof.

It is another object of the present invention to provide an artificial hip joint stem and a stem providing method which allows an inserted stem to be separated such that only a part that is separated during reoperation can be removed or that the entirety of the artificial hip joint stem can be easily removed to reduce time required for operation and reduce pains and side effects accompanying the operation.

Technical Solution

In order to achieve the above object, the present invention is configured as follows.

In accordance with one aspect of the present invention, provided is an artificial hip joint stem used to replace a damaged femoral head or acetabulum, the artificial hip joint stem including a stem body including a head fixing portion protruding from an upper portion of the stem body to fix the head, an operation space having a horizontally opened upper side, and a head insertion hole vertically penetrated so as to be connected to the operation space; screw portion inserted into and rotated in the head insertion hole; a motion converter inserted into the operation space and vertically moved by the screw portion connected thereto; a fixing bracket inserted into the operation space to fix the screw portion such that the screw portion rotates without changing a depth thereof; a variable operation portion inserted into a support surface of the stem body and having a width adjusted in a horizontal direction by operation of the motion converter;

and a movable pin configured to fix the variable operation portion to the motion converter.

An upper end and lower end of the variable operation portion are expanded differently from each other, wherein the upper end of the variable operation portion is expanded more than the lower end thereof.

When the motion converter is lifted and lowered by the screw portion, the motion converter causes the movable pin to make a curved movement through a guide hole thereof.

The movable pin is inclinedly arranged in the motion converter.

The guide hole of the motion converter and an outer circumferential surface of the movable pin are curved in a longitudinal direction.

The guide hole and the movable pin are curved to form a radius in a direction of expansion of the variable operation portion.

The curved movement is determined by the following equations:

$$(x-x_R)^2+(y-y_R)^2-R^2=0 \qquad (1)$$

$$(x-x_R)^2+(y-y_R+u_y)^2-R^2=0 \qquad (2)$$

$$(x_a-x_R)^2+(y_a-y_R)^2-R^2=0 \qquad (3)$$

$$(x_b-x_R)^2+(y_b-y_R)^2-R^2=0 \qquad (4)$$

$$(x_a-x_R)^2+(y_a-y_R+u_y)^2-R^2=0 \qquad (5)$$

$$(x_b-x_R)^2+(y_b-y_R+u_y)^2-R^2=0 \qquad (6)$$

$$(R-e)^2<(x_a-x_R)^2+(y_a-y_R)^2<(R+e)^2; \qquad (7)$$

$$(R-e)^2<(x_b-x_R)^2+(y_b-y_R)^2<(R+e)^2; \qquad (8)$$

$$(R-e)^2<(x_a-x_R)^2+(y_a-y_R+u_y)^2<(R+e)^2; \qquad (9)$$

$$(R-e)^2<(x_b-x_R)^2+(y_b-y_R+u_y)^2<(R+e)^2; \qquad (10)$$

$$|(x_a-x_R)^2+(y_a-y_R)^2-R^2|D2eR; \qquad (11)$$

$$|(x_b-x_R)^2+(y_b-y_R)^2-R^2|D2eR; \qquad (12)$$

$$|(x_a-x_R)^2+(y_a-y_R+u_y)^2-R^2|D2eR; \text{ and} \qquad (13)$$

$$|(x_b-x_R)^2+(y_b-y_R+u_y)^2-R^2|D2eR. \qquad (14)$$

where D is . . . ≤.

The artificial hip joint stem may further include protruding collar arranged at an upper portion of the stem body. Accordingly, the stem body may be seated on the upper-end cross section of the cut femur.

In accordance with another aspect of the present invention, provided is an artificial step providing method using the artificial hip joint stem, the method including inserting the stem body into an upper end of a processed femur; expanding the variable operation portion from the stem body rotating the screw portion of the inserted stem body; and fixing the screw portion so as not to be loosened by an external impact.

The expanding includes converting a rotary motion of the screw portion into a curved movement of the movable pin such that the upper and lower ends of the variable operation unit are expanded to have different widths.

The expanding includes forming and expanding, by the variable operation portion, a curve in a direction of the expanding.

Advantageous Effects

According to the present invention, an artificial hip joint stem to be inserted into the femur has a structure that is separable, contractible and expandable. Accordingly, an impact applied to the femur through the stem can be minimized when the stem is inserted into the femur, and the stem can be easily removed even when it is to be removed.

Further, according to the present invention, since the inserted stem can be contracted and expanded, the step can be easily removed from the femur during reoperation. Accordingly, it is easy to completely remove the artificial hip joint, and therefore the time required for the operation, and the pains and the side effects accompanying the operation can be reduced.

BEST MODE

Hereinafter, preferred embodiments of the present invention will be described in detail with reference to the accompanying drawings. The embodiments of the present invention can be modified in various forms, and the scope of the present invention should not be construed as being limited to the embodiments described below. The embodiments are provided to explain the present invention in detail to those having ordinary skill in the art to which the present invention belongs. Accordingly, the shape of each element shown in the drawings may be exaggerated for a clearer description.

Terms including ordinal numbers such as first, second, etc. may be used to explain various constituents, but the constituents are not limited thereto. These terms are used only for the purpose of distinguishing one constituent from another.

Terms used in this specification are merely adopted to explain specific embodiments, and are not intended to limit the present invention. A singular expression includes a plural expression unless the two expressions are contextually different from each other. In this specification, a term "include" or "have" is intended to indicate that characteristics, figures, steps, operations, constituents, and components disclosed in the specification or combinations thereof exist. The term "include" or "have" should be understood as not pre-excluding possibility of existence or addition of one or more other characteristics, figures, steps, operations, constituents, components, or combinations thereof.

Figure 2:
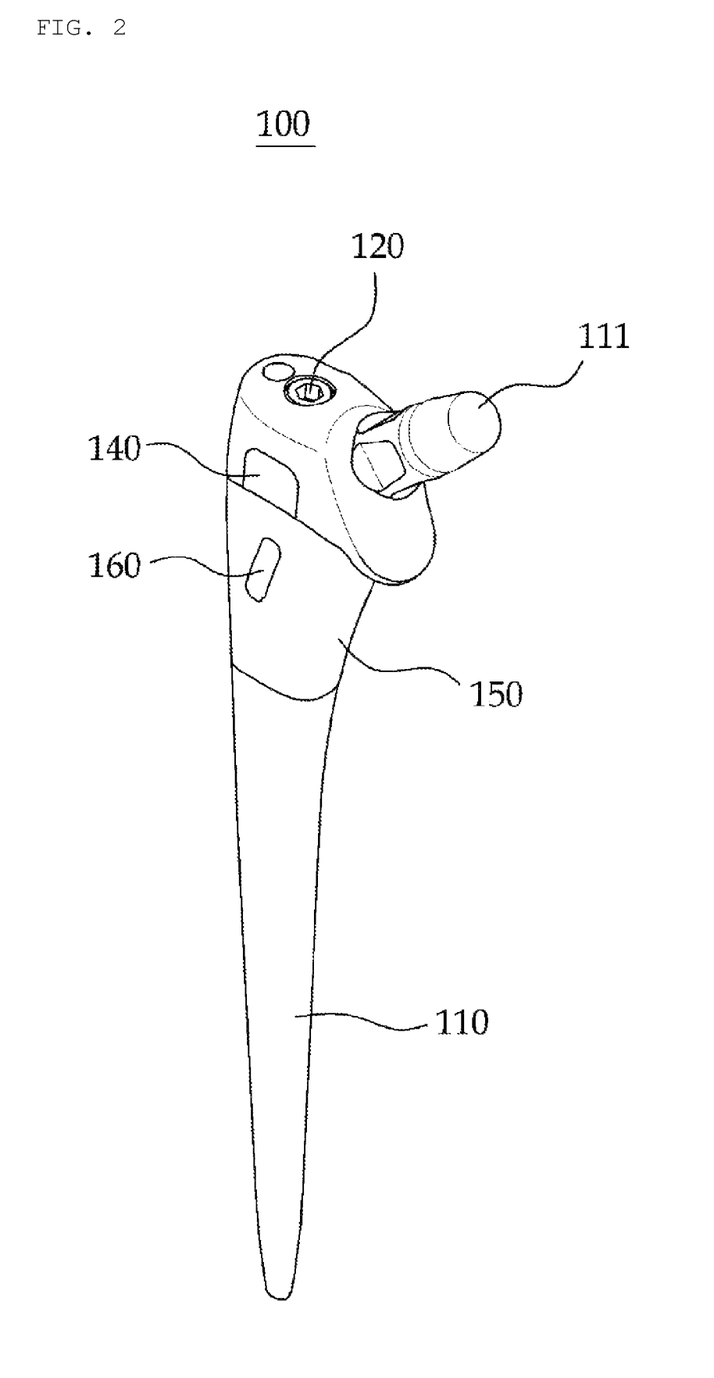
FIG. 2 is a perspective view showing an artificial hip joint stem according to the present invention.
Figure 3:
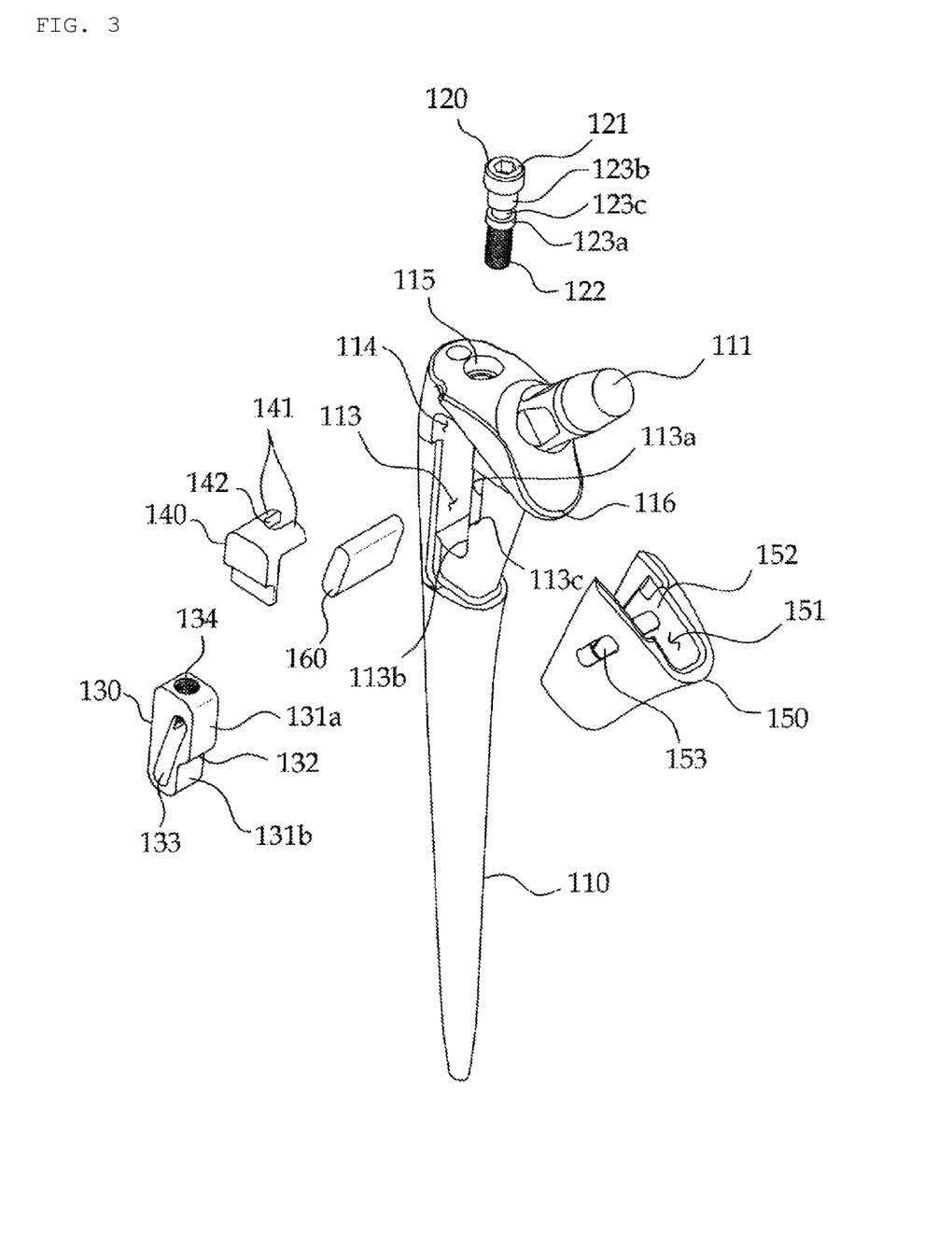
FIG. 3 is an exploded perspective view showing the artificial hip joint stem according to the present invention.

As shown in FIGS. 2 and 3, an artificial hip joint stem 100 of the present invention includes a stem body 110, a screw portion 120, a motion converter 130, a fixing bracket 140, a variable operation portion 150, and a movable pin 160.

The stem body 110 has a predetermined length and is gradually reduced in diameter toward the lower side. The stem body 110 is provided, at an upper end thereof, with a head fixing portion 111 protruding at a predetermined inclination angle to be coupled with a head (not shown).

The stem body 110 is provided with the variable operation portion 150, which is partially cut open at an upper side thereof so as to be detachable. A support surface 112 having a shape corresponding to the variable operation portion 150 is formed on the side of the stem body 110 such that the variable operation portion 150 is slidably coupled thereto. An operation space 113 having a predetermined length is formed to horizontally penetrate the support surface 112. An insertion space 114 is formed to extend upward from the operation space 113. A head insertion hole 115 that is vertically open is formed in an upper portion of the stem body 110 so as to communicate with the insertion space 114.

A collar 116 is further formed at one side of the upper end of the stem body 110 so as to be coupled to and supported by the upper surface of a cut femoral head.

A first guide surface 113a and a second guide surface 113b are formed on one side surface of the operation space 113 in a stepwise manner. A engagement surface 113c is inclinedly formed on the one side surface to connect the first guide surface 113a and the second guide surface 113b.

The screw portion 120 includes a screw head 121 inserted into the head insertion hole 115 of the stem body 110, a male thread 122 formed to have a predetermined length from the screw head 121, steps 123a and 123b formed between the screw head 121 and the male thread 122 in a stepwise manner, and an insertion groove 124 formed between the steps.

The motion converter 130 has a rectangular shape and has stepped sliding surfaces 131a and 131b formed on one outer side thereof, and an engagement surface 132 is formed to inclinedly connect the sliding surfaces 131a and 131b. The inside of the motion converter is provided with a guide hole 133 that is inclined to one side to have a predetermined length and is open in the horizontal direction. The motion converter is also provided with a female screw 134 that is open upward so as to communicate with the guide hole 133.

Here, the guide hole 133 has a curved shape in the inclined direction.

The fixing bracket 140 is disposed in the insertion space 114 and inserted into the insertion groove 124 of the screw portion 120 to support the screw portion. The fixing bracket includes a pair of protrusions 141 and a groove 142 formed between the protrusions.

The variable operation portion 150 is formed by cutting a part of the upper part of the stem body 110 in a square bracket shape, and includes a guide surface 152 formed in the inner insertion space 151 to correspond to the support surface 112 of the stem body 110 and a pair of fixing holes 153 penetrated in the horizontal direction. That is, when the variable operation portion 150 is inserted into the stem body, the outer circumferential surface of the stem body and the outer circumferential surface of the variable operation portion are integrally arranged.

Here, the upper and lower ends of the variable operation portion have a curved shape.

The movable pin 160 has a predetermined length and width and has an elliptical cross-section. Further, the movable pin has a curved shape like the guide hole 133, and thus can slide in the guide hole 133.

According to the coupling configurations as above, the sliding surfaces 131a and 131b of the motion converter 130 are inserted and brought into close contact with the first guide surface 113a and the second guide surface 113b of the operation space 113, and the engagement surface 132 rests on the engagement surface 113c.

In this state, the screw portion 120 may be inserted into the head insertion hole 115 such that the male thread 122 can be screw-coupled to the female thread 134. In addition, the fixing bracket 140 is inserted into the insertion space 114 such that the insertion groove 124 can be positioned in the groove 142 and the upper and lower ends of the protrusions 141 can support the steps 123a and 123b in the insertion groove 124.

At this time, the insertion space 114 is extended from the operation space 113 with one side thereof open in the side surface of the stem body 110 and the other side thereof blocked. Thus, when the fixing bracket 140 is inserted into the insertion space, the protrusions can be tightly fixed to the blocked side.

Next, the variable operation portion 150 is inserted onto the stem body such that the guide surface 152 is brought into close contact with the support surface 112 and thus the guide hole 133 of the motion conversion portion 130 is aligned with the fixing hole 153. Then, the movable pin 160 is inserted and fixed through the fixing hole 153 and the guide hole.

Here, the guide hole 133, the fixing hole 153, and the movable pin 160 are curved and inclined in the direction of the widthwise extension of the variable operation portion 150.

The curved shape of the guide hole, the fixing hole, and the movable pin, and the curve of the upper and lower ends of the variable operation portion will be described in detail below.

The operation state of the present invention will be described, and the installation method of the present invention will be described.

An artificial hip joint step providing method using the artificial hip joint stem according to the present invention includes 1) inserting the stem body into a processed femoral head; 2) expanding the variable operation portion from the stem body by rotating the screw portion of the inserted stem body; and 3) fixing the screw portion to prevent the screw portion from being loosened by an external impact, wherein the operation 2) may include converting a rotary motion of the screw portion into a curved movement of the movable pin such that the upper and lower ends of the variable operation portion have different expansion widths.

In the operation 2), the variable operation portion is expanded while forming a curve in the expanding direction.

Hereinafter, an operation state of the present invention will be described with reference to the accompanying drawings.

Figure 4:
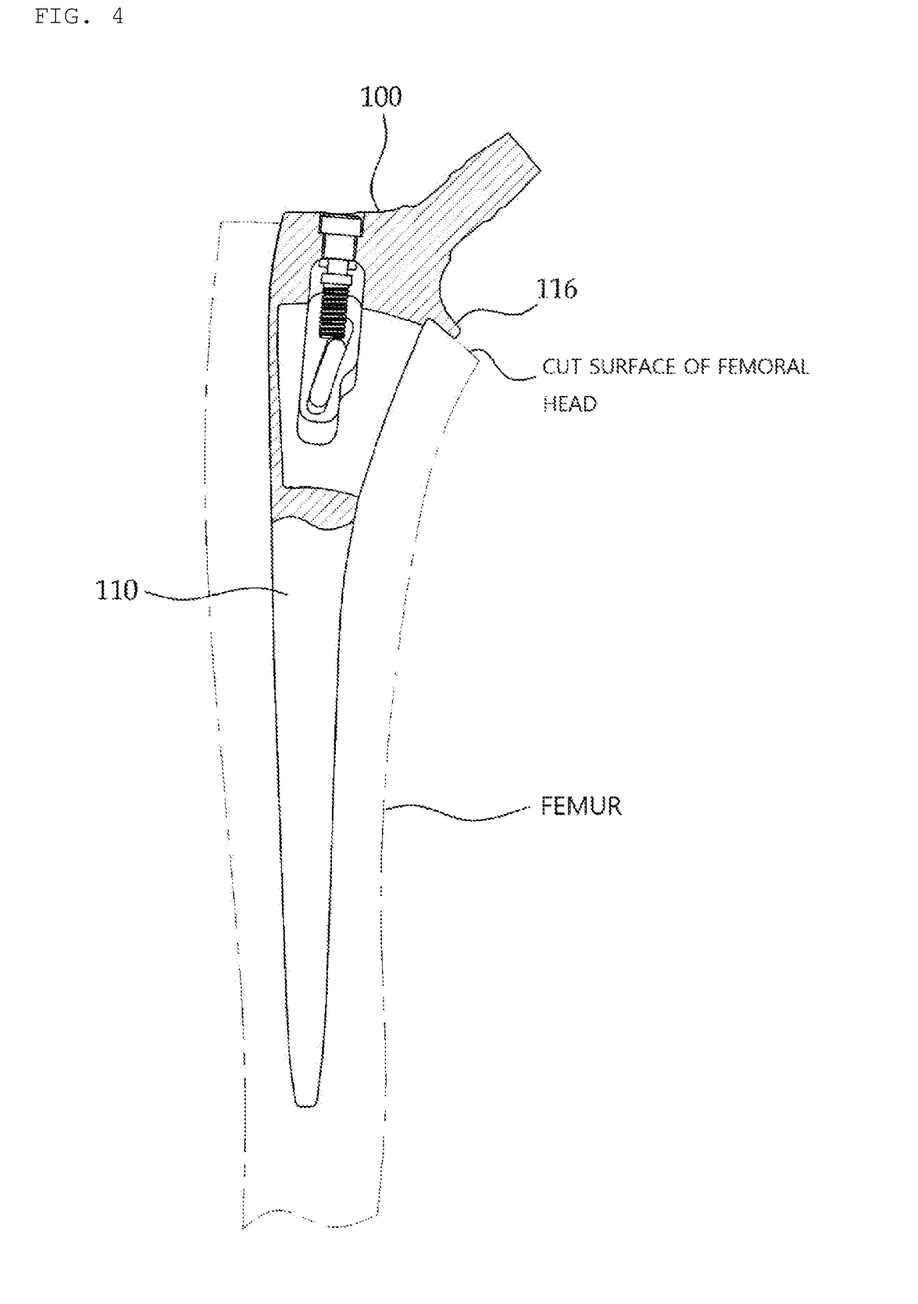
FIGS. 4 and 5 are views showing an installation position of the artificial hip joint stem according to the present invention.

As shown in FIG. 4, a damaged femoral head is cut, and a hole is drilled in the femur to have a certain depth from the femoral head such that the step can be inserted into the hole. Then, the stem is inserted into the hole using a stem insertion tool.

If the inserted stem is inserted so as to closely contact the hole, it can be used as it is. However, the stem has a curved wedge shape. Often, the stem is partially or entirely loosely inserted into the hole.

That is, drilling a hole having the same or similar size as the shape of the stem in a surgical procedure is very difficult and requires a high skill, and accordingly a hole larger than the stem is usually formed.

Figure 5:
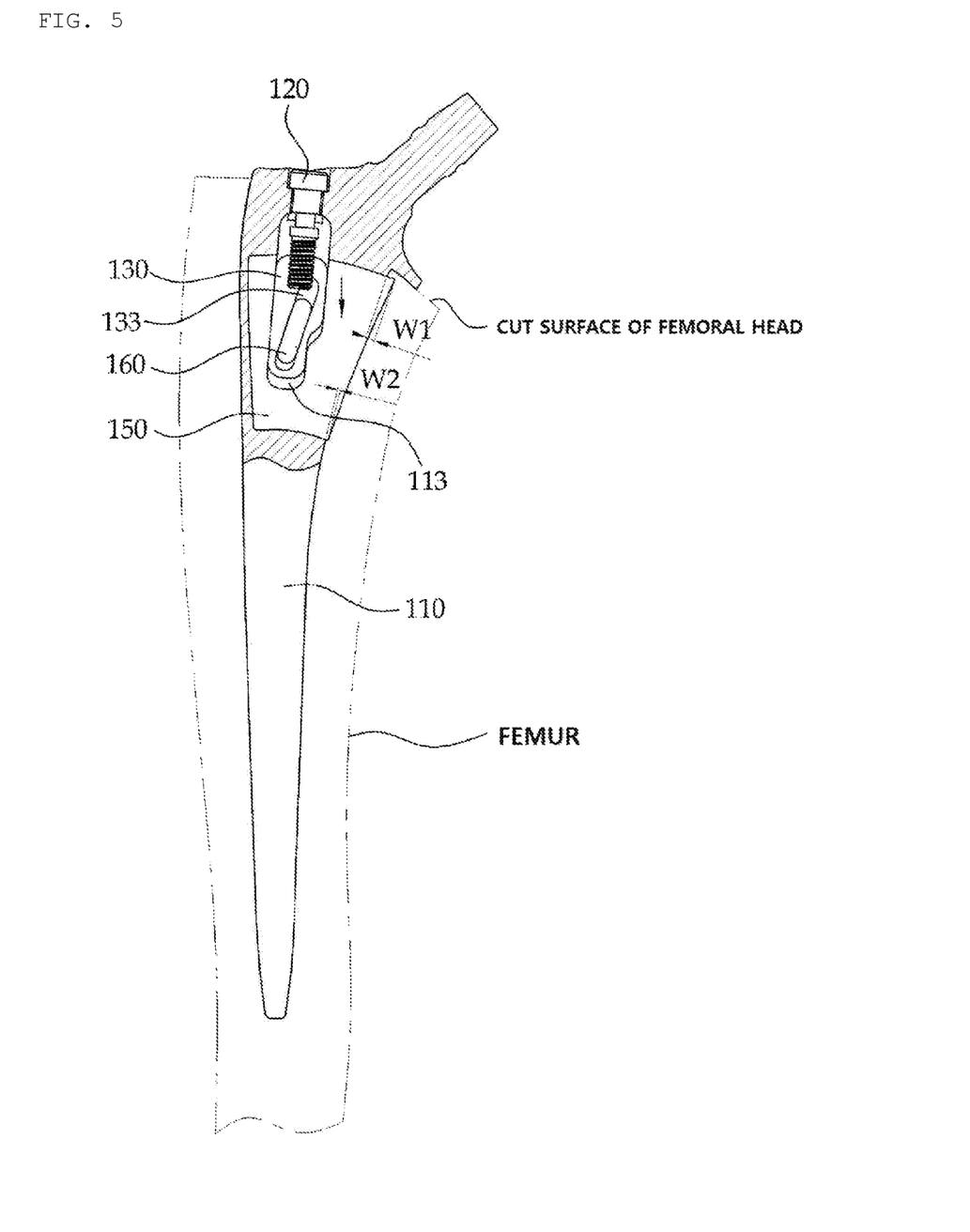

When the hole is formed to have a larger size than the stem, the stem cannot be employed. Accordingly, as shown in FIG. 5, the screw portion 120 disposed in the upper portion of the inserted stem is rotated to convert the rotary motion of the screw portion 120 into vertical movement of the screw-coupled motion converter 130. Then, as the motion converter 130 descends, the variable pin 160 inserted into the guide hole 133 and fixed to the variable operation portion 150 is slidably moved in the guide hole to outwardly push the variable operation portion 150 connected to the movable pin widthwise such that the variable operation portion 150 protrudes from the outer circumferential surface of the stem body 110.

Here, since each of the upper and lower ends of the protruded variable operation portion 150 has a curved shape, and the movable pin and the guide hole also have curved shape, the variable operation portion moves along a curve by a distance as the movable pin moves along the curve of the guide hole. Thus, the protrusion width W1 of the upper end of the variable operation portion is greater than the protrusion width W2 of the lower end thereof. Thereby, the stem body 110 can be expanded to fit the size of the hole while maintaining the curved shape of the circumferential surface of the stem body.

Here, a collar 116 may be further provided at one side of the upper portion of the stem body so as to be in close contact with and supported by the upper surface of the cut femur.

That is, as the screw portion is rotated, the motion converter vertically slides and descends in the operation space 113. Then, the movable pin slides in the guide hole by the movement distance of the descending motion converter. Since each of the movable pin and the guide hole has a curved shape, the variable operation portion connected to the movable pin makes a curve motion corresponding to the curved movement of the movable pin, thereby expanding the stem body outward.

In order to perform such operation, the movable pin and the guide hole should be formed in a curved shape to have a radius in the direction of expansion of the variable operation portion, and the upper and lower ends of the variable operation portion should have a corresponding curved shape.

In order for the curve motions to occur without interfering with each other, the equations given below should be satisfied.

Figure 6:
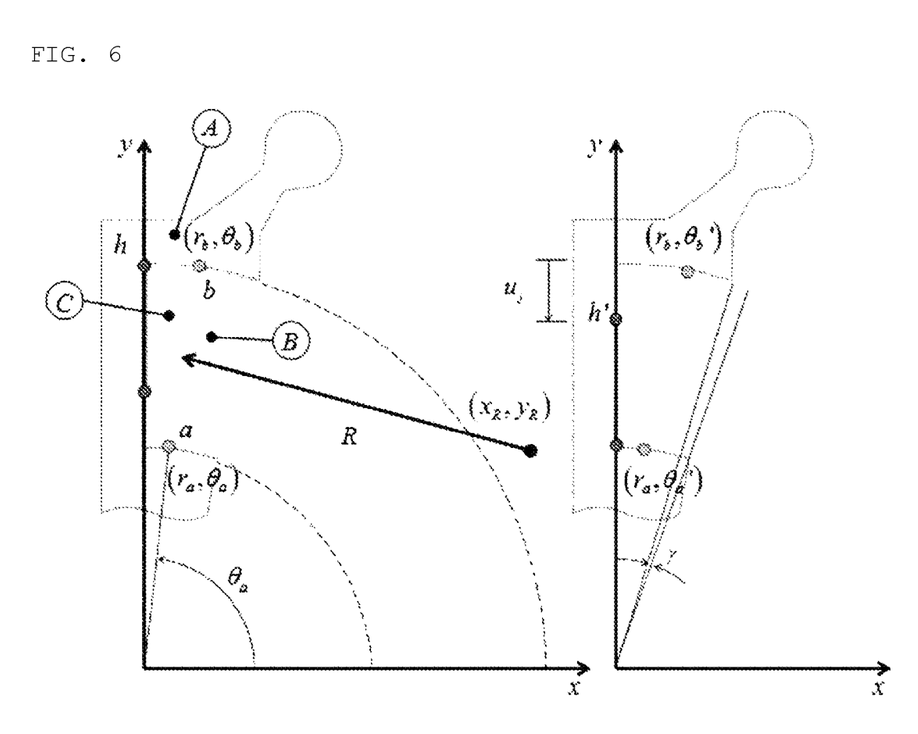
FIG. 6 is a view illustrating an operation principle of the artificial hip joint stem according to the present invention.

The equations are described with reference to FIG. 6. In FIG. 6, "A" denotes the stem body, "B" denotes the variable operation portion, and "C" denotes the movable pin, the guide hole, and the motion converter. For simplicity, the elements will be represented by "A", "B" and "C" in the following description.

As shown in FIG. 6, special inclined surfaces rotate around the origin of the coordinates. In "B", when the position of the lower end of the contact surface is a, and the position of the upper end of the contact surface is b, the coordinates of each position can be represented by $(r_a, \theta_a)$ and $(r_b, \theta_b)$ in the cylindrical coordinate system. When the coordinates of the positions a' and b' to which "B" is to be moved by rotating by r due to vertical movement of "C" are defined as $(r_a, \theta'_a)$ and $(r_b, \theta'_b)$, respectively, the relationship between a, b and a', b' is defined as follows:

$$\theta'_a = \theta_a - \gamma,$$

$$\theta'_b = \theta_b - \gamma.$$

In addition, the contact surface at a position where "B" does not expand can be represented by a circle given by the following equation:

$$(x-x_R)^2+(y-y_R)^2-R^2=0. \tag{1}$$

When "C" moves by $u_y$ in the (−)y direction, the moved contact surface can be represented by the following equation:

$$(x-x_R)^2+(y-y_R+u_y)^2-R^2=0. \tag{2}$$

When "B" and "C" are in contact with each other before the expansion, the two points a and b satisfy the circle equation. When the points a and b defined in the cylindrical coordinate system are represented in the Cartesian coordinate system, the circles are represented by rectangular coordinates, they can be expressed as follows:

$$a=[x_a,y_a]=[r_a \cos(\theta_a), r_a \sin(\theta_a)],$$

$$b=[x_b,y_b]=[r_b \cos(\theta_b), r_b \sin(\theta_b)].$$

The positions after the expansion can be expressed as follows:

$$a'=[x_{a'},y_{a'}]=[r_a \cos(\theta_a-\gamma), r_a \sin(\theta_a-\gamma)],$$

$$b'=[x_{b'},y_{b'}]=[r_b \cos(\theta_b-\gamma), r_b \sin(\theta_b-\gamma)].$$

$[x_a, y_a]$ and $[x_b, y_b]$ should satisfy Equation (1), and $[x_{a'}, y_{a'}]$ and $[x_{b'}, y_{b'}]$ should satisfy Equation (2).

$$(x_a-x_R)^2+(y_a-y_R)^2-R^2=0. \tag{3}$$

$$(x_b-x_R)^2+(y_b-y_R)^2-R^2=0. \tag{4}$$

$$(x_{a'}-x_R)^2+(y_{a'}-y_R+u_y)^2-R^2=0. \tag{5}$$

$$(x_{b'}-x_R)^2+(y_{b'}-y_R+u_y)^2-R^2=0. \tag{6}$$

Therefore, for the artificial hip joint stem, which is configured to expand by rotating about the origin of coordinates by r, the points a, b, and R should be determined to satisfy Equations (3) to (6).

At points a and b, $r_a$, $\theta_a$, and $r_b$ are variables for determining the size of the variable operation portion and may be determined by the intention of the designer.

Once $r_a$, $\theta_a$, and $r_b$ are determined, $\theta_b$ and R should be determined to ensure the contact after the expansion.

This engineering problem may be to find variables $\theta_b$ and R that satisfy four equations at the same time. However, it is substantially impossible to mathematically find the correct answer. Accordingly, for the artificial hip joint, which is a structure formed by coupling between metal members, if the mathematical error is smaller than the mechanical error that allows metal members to be coupled so as to be operable in contact with each other, the structure can be sufficiently mechanically operated even if there is a mathematical error. Therefore, in the case of the artificial hip joint, only corresponding values need to be estimated from the equations. Here, when the allowable error for assembly is "e", applying "e" to Equations (3) to (6) may yield the following equations:

$$(R-e)^2 < (x_a-x_R)^2+(y_a-y_R)^2 < (R+e)^2, \tag{7}$$

$$(R-e)^2 < (x_b-x_R)^2+(y_b-y_R)^2 < (R+e)^2, \tag{8}$$

$$(R-e)^2 < (x_{a'}-x_R)^2+(y_{a'}-y_R+u_y)^2 < (R+e)^2, \text{ and} \tag{9}$$

$$(R-e)^2 < (x_{b'}-x_R)^2+(y_{b'}-y_R+u_y)^2 < (R+e)^2. \tag{10}$$

In Equation (7), $e^2 \ll 2Re$. Accordingly, when $e^2$ is ignored, Equations (7) to (10) can be represented by Equations (11) to (14) below:

$$|(x_a-x_R)^2+(y_a-y_R)^2-R^2| \unlhd 2eR, \quad (11)$$

$$|(x_b-x_R)^2+(y_b-y_R)^2-R^2| \unlhd 2eR, \quad (12)$$

$$|(x_a-x_R)^2+(y_a-y_R+u_y)^2-R^2| \unlhd 2eR, \text{ and} \quad (13)$$

$$|(x_b-x_R)^2+(y_b-y_R+u_y)^2-R^2| \unlhd 2eR. \quad (14)$$

Here, D is . . . ≤.

Figure 7:
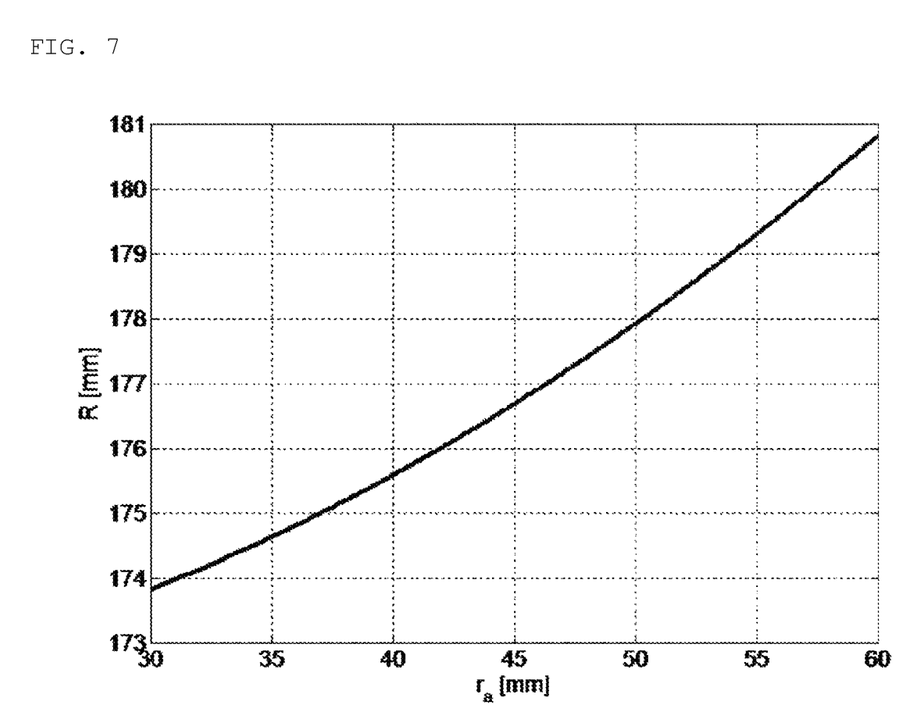
FIG. 7 is a graph depicting a radius of curvature for a curved motion according to the artificial hip joint stem according to the present invention.

$\theta_b$ and R that satisfy Equations (11) to (14), can be calculated through numerical analysis and thus a graph as shown in FIG. 7 can be derived. Accordingly, the operation of the variable operation portion can be derived by determining the magnitude of R constituting contact points a and b between "B" and "C".

As described above, the outer circumferential surface of the stem can be expanded through the guide hole, the movable pin, and the variable operation portion, which have a curved surface and make movements according to the curved surface. In addition, as the degree of expansion differs between the lower and upper ends of the stem, the inserted stem can be more precisely and securely fixed in the hole.

Further, when the inserted stem is replaced, the expanded variable operation portion can be contracted and released from the close contact. Thereby, the stem can be more effectively replaced.

While the present invention has been particularly shown and described with reference to exemplary embodiments thereof, it is to be understood that the embodiments are intended to provide understanding of the present invention and are not intended to limit the scope of the invention.

It will be apparent to those skilled in the art that various modifications and variations can be made in the present invention without departing from the spirit and scope of the invention. Thus, it is intended that the present invention cover the modifications and variations of this invention provided they come within the scope of the appended claims and their equivalents.

The invention claimed is:

1. An artificial hip joint stem used to replace a damaged femoral head or acetabulum, the artificial hip joint stem comprising:
a stem body comprising a head fixing portion protruding from an upper portion of the stem body to fix the head, an operation space having a horizontally opened upper side of the stem body, and a head insertion hole vertically penetrated so as to be connected to the operation space;
a screw portion inserted into and rotated in the head insertion hole;
a motion converter inserted into the operation space and vertically moved by the screw portion connected of the motion converter;
a fixing bracket inserted into the operation space to fix the screw portion such that the screw portion rotates without changing a depth thereof;
a variable operation portion inserted into a support surface of the stem body and having a width adjusted in a horizontal direction by operation of the motion converter; and
a movable pin configured to fix the variable operation portion to the motion converter.

2. The artificial hip joint stem according to claim 1, wherein an upper end and a lower end of the variable operation portion are expanded differently from each other.

3. The artificial hip joint stem according to claim 2, wherein the upper end of the variable operation portion is expanded more than the lower end of the variable operation.

4. A artificial hip joint step providing method using the artificial hip joint stem according to claim 3, the method comprising:
inserting the stem body into an upper end of a processed femur;
expanding the variable operation portion from the stem body by rotating the screw portion of the inserted stem body; and
fixing the screw portion so as not to be loosened by an external impact.

5. A artificial hip joint step providing method using the artificial hip joint stem according to claim 2, the method comprising:
inserting the stem body into an upper end of a processed femur;
expanding the variable operation portion from the stem body by rotating the screw portion of the inserted stem body; and
fixing the screw portion so as not to be loosened by an external impact.

6. The artificial hip joint stem according to claim 1, wherein, when the motion converter is lifted and lowered by the screw portion, the motion converter causes the movable pin to make a curved movement through a guide hole of the motion converter.

7. The artificial hip joint stem according to claim 6, wherein the movable pin is inclinedly arranged in the motion converter.

8. A artificial hip joint step providing method using the artificial hip joint stem according to claim 7, the method comprising:
inserting the stem body into an upper end of a processed femur;
expanding the variable operation portion from the stem body by rotating the screw portion of the inserted stem body; and
fixing the screw portion so as not to be loosened by an external impact.

9. The artificial hip joint stem according to claim 6, wherein the guide hole of the motion converter and an outer circumferential surface of the movable pin are curved in a longitudinal direction.

10. The artificial hip joint stem according to claim 9, wherein the guide hole and the movable pin are curved to form a radius in a direction of expansion of the variable operation portion.

11. A artificial hip joint step providing method using the artificial hip joint stem according to claim 10, the method comprising:
inserting the stem body into an upper end of a processed femur;
expanding the variable operation portion from the stem body by rotating the screw portion of the inserted stem body; and
fixing the screw portion so as not to be loosened by an external impact.

12. A artificial hip joint step providing method using the artificial hip joint stem according to claim 9, the method comprising:
inserting the stem body into an upper end of a processed femur;

expanding the variable operation portion from the stem body by rotating the screw portion of the inserted stem body; and fixing the screw portion so as not to be loosened by an external impact.

13. The artificial hip joint stem according to claim 6, wherein the curved movement is determined by the following equations:

$$(x-x_R)^2+(y-y_R)^2-R^2=0 \tag{1}$$

$$(x-x_R)^2+(y-y_R+u_y)^2-R^2=0 \tag{2}$$

$$(x_a-x_R)^2+(y_a-y_R)^2-R^2=0 \tag{3}$$

$$(x_b-x_R)^2+(y_b-y_R)^2-R^2=0 \tag{4}$$

$$(x_a-x_R)^2+(y_a-y_R+u_y)^2-R^2=0 \tag{5}$$

$$(x_b-x_R)^2+(y_b-y_R+u_y)^2-R^2=0 \tag{6}$$

$$(R-e)^2<(x_a-x_R)^2+(y_a-y_R)^2<(R+e)^2; \tag{7}$$

$$(R-e)^2<(x_b-x_R)^2+(y_b-y_R)^2<(R+e)^2; \tag{8}$$

$$(R-e)^2<(x_a-x_R)^2+(y_a-y_R+u_y)^2<(R+e)^2; \tag{9}$$

$$(R-e)^2<(x_b-x_R)^2+(y_b-y_R+u_y)^2<(R+e)^2; \tag{10}$$

$$|(x_a-x_R)^2+(y_a-y_R)^2-R^2| D 2eR; \tag{11}$$

$$|(x_b-x_R)^2+(y_b-y_R)^2-R^2| D 2eR; \tag{12}$$

$$|(x_a-x_R)^2+(y_a-y_R+u_y)^2-R^2| D 2eR; \text{ and} \tag{13}$$

$$|(x_b-x_R)^2+(y_b-y_R+u_y)^2-R^2| D 2eR \tag{14}$$

where D is ≤.

14. A artificial hip joint step providing method using the artificial hip joint stem according to claim 13, the method comprising:

inserting the stem body into an upper end of a processed femur;

expanding the variable operation portion from the stem body by rotating the screw portion of the inserted stem body; and fixing the screw portion so as not to be loosened by an external impact.

15. A artificial hip joint step providing method using the artificial hip joint stem according to claim 6, the method comprising:

inserting the stem body into an upper end of a processed femur;

expanding the variable operation portion from the stem body by rotating the screw portion of the inserted stem body; and fixing the screw portion so as not to be loosened by an external impact.

16. The artificial hip joint stem according to claim 1, further comprising:

a protruding collar arranged at an upper portion of the stem body.

17. A artificial hip joint step providing method using the artificial hip joint stem according to claim 16, the method comprising:

inserting the stem body into an upper end of a processed femur;

expanding the variable operation portion from the stem body by rotating the screw portion of the inserted stem body; and fixing the screw portion so as not to be loosened by an external impact.

18. A artificial hip joint step providing method using the artificial hip joint stem according to claim 1, the method comprising:

inserting the stem body into an upper end of a processed femur;

expanding the variable operation portion from the stem body by rotating the screw portion of the inserted stem body; and fixing the screw portion so as not to be loosened by an external impact.

19. The method according to claim 18, wherein the expanding comprises:

converting a rotary motion of the screw portion into a curved movement of the movable pin such that the upper and lower ends of the variable operation unit are expanded to have different widths.

20. The method according to claim 18, wherein the expanding comprises:

forming and expanding, by the variable operation portion, a curve in a direction of the expanding.

* * * * *